US00PP18285P3

(12) United States Plant Patent
Eggleton

(10) Patent No.: US PP18,285 P3
(45) Date of Patent: Dec. 4, 2007

(54) ***NEMESIA* PLANT NAMED 'CONFETTI FROSTED PINK'**

(50) Latin Name: *Nemesia×hybrida*
Varietal Denomination: Confetti Frosted Pink

(76) Inventor: Steven Eggleton, 3 Harris Road, Wonga Park, Melbourne, Vic (AU), 3115

( * ) Notice: Subject to any disclaimer, the term of this patent is extended or adjusted under 35 U.S.C. 154(b) by 32 days.

(21) Appl. No.: 11/435,470

(22) Filed: May 16, 2006

(65) Prior Publication Data

US 2006/0282925 P1 Dec. 14, 2006

(30) Foreign Application Priority Data

Jun. 9, 2005 (AU) ..... 2005/172

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

UPOV ROM GTITM Computer Database, GTI Jouve Retrieval Software 2006/04 Citation for 'Confetti Frosted Pink'.*

* cited by examiner

*Primary Examiner*—Wendy C. Haas

(57) ABSTRACT

A new and distinct cultivar of *Nemesia* plant named 'CONFETTI FROSTED PINK' that is characterized by dense compact habit, light green and cream-white variegated foliage, and pink flowers with yellow centers. In combination these characteristics set 'CONFETTI FROSTED PINK' apart from all other existing varieties of *Nemesia* known to the inventor.

2 Drawing Sheets

Genus: *Nemesia.*
Species. *×hybrida.*
Denomination: 'CONFETTI FROSTED PINK'.

BACKGROUND OF THE INVENTION

The present invention relates to a new and distinct cultivar of *Nemesia* plant grown as an ornamental plant for use in container, and as a bedding or patio plant. The new variety is known botanically as *Nemesia×hybrida* and will be referred to hereinafter by the cultivar name 'CONFETTI FROSTED PINK'.

The new *Nemesia* cultivar named 'CONFETTI FROSTED PINK' was discovered as a branch sport on an individual plant within a commercial crop of *Nemesia* 'Confetti Bright Pink' (unpatented). The crop was growing in a cultivated area of Wonga Park, Victoria, Australia. The inventor discovered 'CONFETTI FROSTED PINK' in November 2002. Selection criteria were variegated foliage, habit, and length of flowering.

The distinguishing characteristics of 'CONFETTI FROSTED PINK' are dense compact habit, light green and cream-white variegated foliage, and pink flowers with yellow centers. 'CONFETTI FROSTED PINK' carries clusters of white buds during the blooming period from spring to fall.

'CONFETTI FROSTED PINK' was first asexually propagated by the inventor in February 2003 in a cultivated area of Victoria, Australia. The method of asexual propagation used was stem cuttings. The inventor has determined that 'CONFETTI FROSTED PINK' is stable and reproduces true to type in successive generations of asexual reproduction.

SUMMARY OF THE INVENTION

The following traits have been repeatedly observed and represent the distinguishing characteristics of 'CONFETTI FROSTED PINK'. In combination these traits set the new cultivar apart from all other existing varieties of *Nemesia* known to the inventor. 'CONFETTI FROSTED PINK' has not been tested under all possible conditions and phenotypic differences may be observed with variations in environmental, climatic, and cultural conditions, without however, any variance in genotype.

1. 'CONFETTI FROSTED PINK' exhibits dense compact habit.
2. 'CONFETTI FROSTED PINK' exhibits pink flowers with yellow centers.
3. 'CONFETTI FROSTED PINK' carries cluster of white buds during the blooming period from spring to fall.
4. 'CONFETTI FROSTED PINK' exhibits light green and cream-white variegated foliage.
5. 'CONFETTI FROSTED PINK' is floriferous and long blooming with large, repeat-flowering heads.
6. 'CONFETTI FROSTED PINK' produces minimal to nil seed set.
7. 'CONFETTI FROSTED PINK' is hardy to USDA Zone 9.
8. 'CONFETTI FROSTED PINK' is grown for use in container, and as a bedding and patio plant.

BRIEF DESCRIPTION OF THE DRAWINGS

The accompanying color drawings illustrate the overall appearance of the new *Nemesia* cultivar named 'CONFETTI FROSTED PINK' showing the colors as true as it is reasonably possible to obtain in colored reproductions of this type. Colors in the drawings may differ from the color values cited in the detailed botanical description, which accurately describe the actual colors of the new variety 'CONFETTI FROSTED PINK'. The drawings have been made from plants which are approximately 12-months-old, in two-litre containers and were grown and which have been grown out of doors in Victoria, Australia.

The drawing labeled

The drawing labeled

BOTANICAL DESCRIPTION OF THE PLANT

Figure 1:
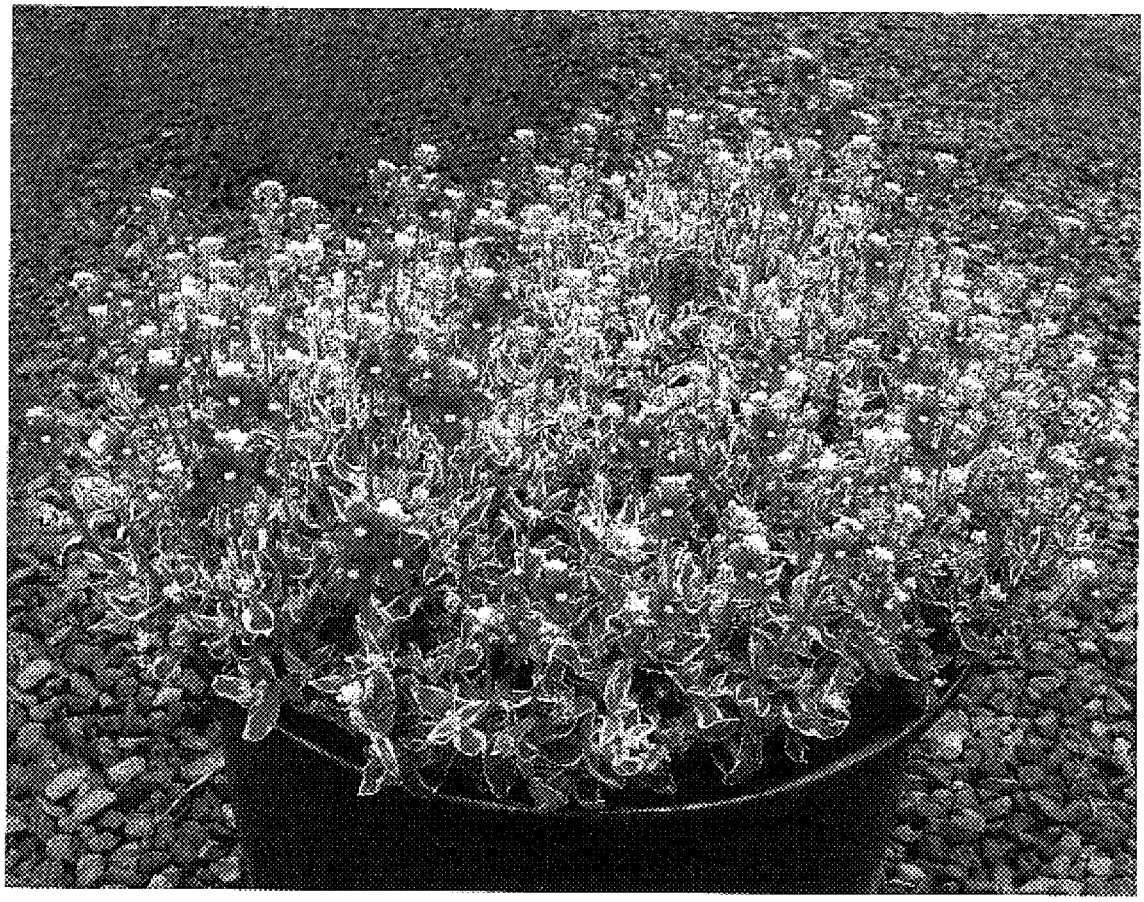
FIG. 1 depicts a whole plant, illustrating habit and variegated foliage from a side perspective.
Figure 2:
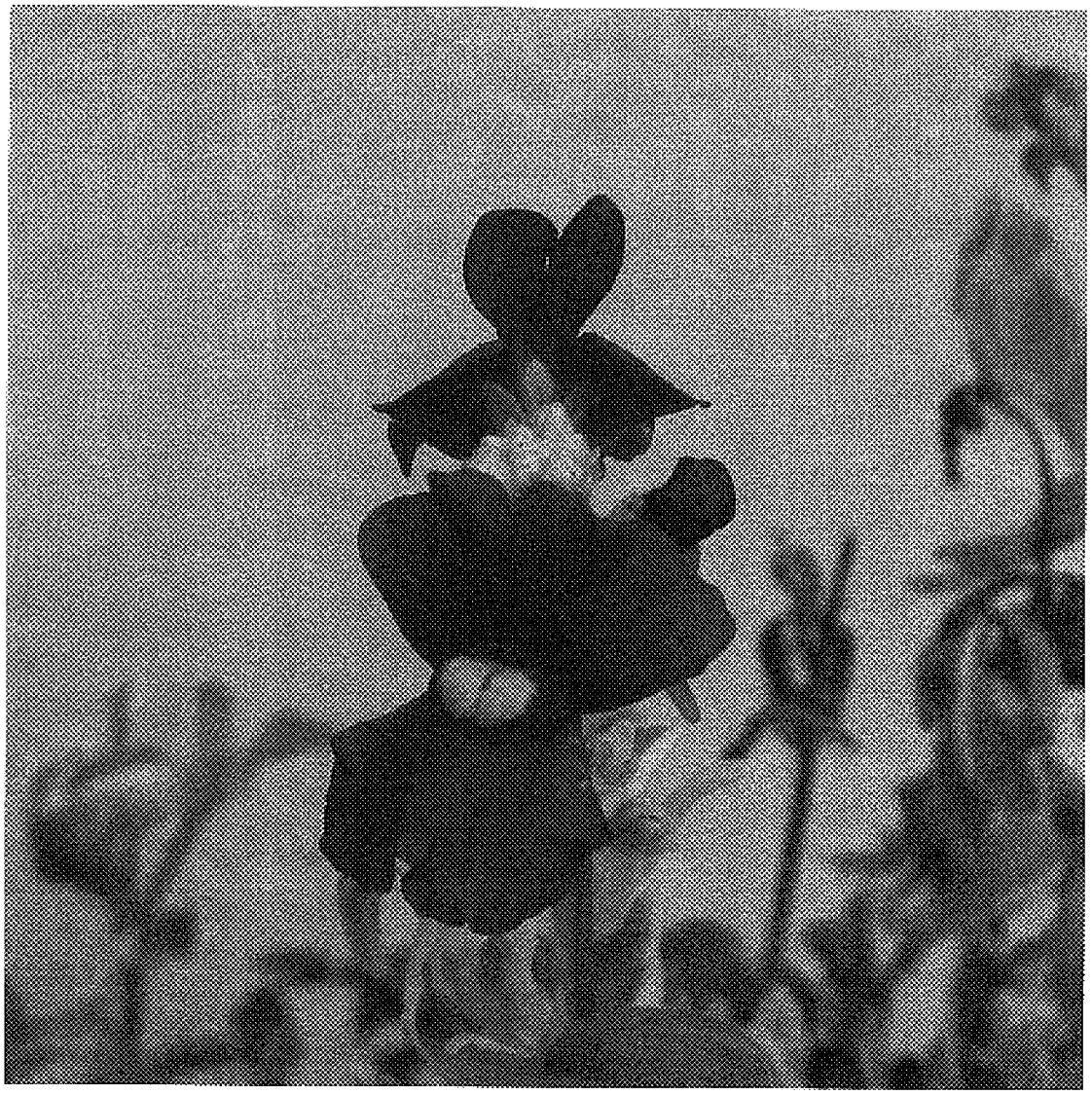
FIG. 2 depicts a close-up view of the flower. Drawings were made using conventional techniques, and although colors may appear different from actual colors due to light reflectance, they are as accurate as possible by conventional photography.

The following is a detailed description of the new *Nemesia* cultivar named 'CONFETTI FROSTED PINK'. Data was collected in Arroyo Grande, Calif. from 6-month-old plants grown indoors in 18 cm. containers. Phenotypic differences may be observed with variations in environmental, climatic, and cultural conditions, without however, any genotypic differences. The color determinations are in accordance with The 2001 Royal Horticultural Society Colour Chart of London, England except where general color terms of ordinary dictionary significance are used. The growing requirements are similar to that of other *Nemesia* plants.

*Botanical classification.*—*Nemesia*×*hybrida* 'CONFETTI FROSTED PINK'.
*Genus.*—*Nemesia.*
*Species:* ×*hybrida.*
*Denomination.*—'CONFETTI FROSTED PINK'.
*Common name.*—Nemesia.
*Plant use.*—Grown for use in containers, as a bedding plant, and patio plant.
*Parentage.*—*Nemesia*×*hybrida* 'CONFETTI FROSTED PINK' was discovered as a branch spot on an individual plant within a commercial crop of *Nemesia* 'Confetti Bright Pink'. The parent is an individual *Nemesia* 'Confetti Bright Pink'.
*Asexual plant propagation.*—Asexual propagation is accomplished using the method of stem cuttings.
*Plant habit.*—Dense compact habit.
*Plant height* (*at maturity*).—30 cm. in height.
*Plant width* (*at maturity*).—60 cm. in width.
Plant type: Perennial herb.
Cultural requirements: Full sun to partial shade, moderate water, and well draining soil.
Time to initiate roots: Ranges from 2–4 weeks at temperatures of 21° Centigrade.
Crop time: Range of 6–9 months to produce a finished 1-litre container plant from a rooted cutting.
Seasonal interest: Pink flowers with yellow centers and clusters of white buds.
Root system: Numerous fine roots.
Plant hardiness: USDA Zone 9.
Disease and pest susceptibility: There are no disease or pest problems known to the inventor other than those commonly affecting *Nemesia.*
Stem:
- *Stem shape.*—Quadrilateral in shape.
- *Stem length.*—16 cm. in length.
- *Stem diameter.*—2.50 mm. in diameter.
- *Stem surface.*—Glabrous.
- *Stem color.*—138B.
- *Internode length.*—Ranges from 1.25 cm to 2.25 cm. on an individual plant.
- *Branching.*—Densely branching.

Foliage:
- *Stipules.*—None observed.
- *Leaf shape.*—Oblanceolate with slightly revolute edges.
- *Leaf division.*—Simple.
- *Leaf apex.*—Acute.
- *Leaf base.*—Rounded.
- *Leaf margin.*—Serrate.
- *Leaf texture.*—Soft and flexible.
- *Leaf surfaces* (*adaxial and abaxial*).—Glabrous.
- *Leaf arrangement.*—Opposite.
- *Leaf length.*—A range of 1 cm. to 3 cm. in length on an individual plant.
- *Leaf width.*—A range of 0.50 cm. to 1.75 cm. in width on an individual plant.
- *Leaf color* (*adaxial surface*).—Colors 138A and 155A are individual present.
- *Leaf color* (*abaxial surface*).—Colors 138B and 155A are individually present.
- *Leaf attachment.*—A combination of sheathing and petiolate is present on an individual stem.
- *Petiole dimensions.*—2 mm. in length and 0.75 mm. in diameter.
- *Petiole shape.*—Sulcate.
- *Petiole color.*—138B.
- *Petiole surface.*—Glabrous.
- *Vein pattern.*—Pinnate vein pattern.
- *Vein color* (*adaxial surface*).—138A.
- *Vein color* (*abaxial surface*).—138B.

Flowers:
- *Type of inflorescence.*—Short terminal raceme.
- *Inflorescence dimensions.*—2 cm. in length and 3 cm. in width.
- *Flowering season.*—Spring, summer and fall.
- *Self-cleaning or persistent.*—Self-cleaning.
- *Pedicel length.*—Ranges from 0.50 mm. to 0.75 mm. in length.
- *Pedicel diameter.*—Less than 0.50 mm. in diameter.
- *Pedicel surface.*—Stipitate glandular.
- *Pedicel color.*—138D.
- *Peduncle length.*—5 cm. in length.
- *Peduncle diameter.*—2 mm. in diameter.
- *Peduncle shape.*—Quadrilateral in shape.
- *Peduncle surface.*—Stipitate glandular.
- *Peduncle color.*—138A.
- *Bud shape.*—Globular.
- *Bud color.*—155A turning to 71A.
- *Bud length.*—Ranges from 7 mm–11 mm. in length.
- *Bud width.*—Ranges from 2 mm.–6 mm. in width.
- *Bud surface.*—Stipitate glandular.
- *Bud quantity.*—A range of 12–15 buds per cluster.
- *Flower color.*—Colors 3B, 70B, 71A are individually present on an individual flower.
- *Flower shape.*—Personate.
- *Flower depth.*—1.50 cm. in depth.
- *Flower length.*—1.75 cm. in length.
- *Flower width.*—2.0 cm. in width.
- *Lower lip dimensions.*—1.25 cm. in width and 1 cm. in length.
- *Lobe* (*lower lip*).—Bilabiate.
- *Upper lip dimensions.*—2 cm. in width and 7 mm. in length.
- *Lobes* (*upper lip*).—4 in number.

*Lobe dimensions* (*each lobe of upper lip*).—7 mm. in length and 5 mm. in width.
*Lip surface.*—Glabrous.
*Lip margin.*—Entire.
*Lip apex* (*upper and lower lips*).—Obcordate.
*Lip base* (*upper lip and lower lips*).—Truncate.
*Lips.*—Two in number.
*Lobes.*—The upper lip has four lobes and the lower lip is bilabiate.
*Lips fused or unfused.*—Basally fused.
*Color of upper lip* (*adaxial surface*).—70B.
*Color of upper lip* (*abaxial surface*).—70D.
*Color of lower lip* (*adaxial surface*).—A combination of colors 84B and 84C.
*Color of lower lip* (*abaxial surface*).—A combination of colors 84B and 84C.
*Palate color.*—3B.
*Palate width.*—4 mm. in width.
*Nectary color.*—3B.
*Nectary surface.*—Lanate.
*Flower spur dimensions.*—0.50 cm. in length and 2 mm in diameter.
*Spur color.*—70B.
*Calyx dimensions.*—7 mm. in diameter.
*Calyx shape.*—Stellate in shape.
*Sepals.*—Five in number.
*Sepal dimensions.*—3 mm. in length and 1.50 mm. in width.
*Sepal surface* (*adaxial surface*).—Stipitate glandular.
*Sepal surface* (*abaxial surface*).—Stipitate glandular.
*Sepal apex.*—Acute apex.
*Sepal base.*—Truncate base.
*Sepal margin.*—Entire.
*Sepal color* (*adaxial surface*).—Colors 138B and 155A are individually present on an individual sepal.
*Sepal color* (*abaxial surface*).—Colors 138B and 155A are individually present on an individual sepal.
*Lastingness of individual flower.*—An individual flower lasts for an average of 5 days.
*Flower fragrance.*—None observed.

Reproductive organs.
*Stamens.*—Two in number.
*Stamen color.*—155A.
*Stamen dimensions.*—3 mm. in length and less than 1 mm. in diameter.
*Anther color.*—161C.
*Anther dimensions.*—Less than 0.50 mm. in length and less than 0.50 mm. in width.
*Pollen quantity.*—Moderate.
*Pollen color.*—161C.
*Pistil.*—1 in number.
*Pistil color.*—155A.
*Pistil dimensions.*—0.25 mm. in length and 0.25 mm. in diameter.
*Ovary dimensions.*—0.50 mm. in length and 0.50 mm. in width.
*Ovary shape.*—Round in shape.
*Ovary position.*—Superior.
*Ovary color.*—145A.

Seed production: No seed has been observed to date.

What is claimed is:

1. A new and distinct cultivar of *Nemesia* plant named 'CONFETTI FROSTED PINK' as described and illustrated herein.

* * * * *